United States Patent
Sakas et al.

(10) Patent No.: US 9,974,618 B2
(45) Date of Patent: May 22, 2018

(54) METHOD FOR DETERMINING AN IMAGING SPECIFICATION AND IMAGE-ASSISTED NAVIGATION AS WELL AS DEVICE FOR IMAGE-ASSISTED NAVIGATION

(71) Applicants: Medcom Gesellschaft für medizinische Bildverarveitung mbH, Darmstadt (DE); ESAOTE S.p.A., Genoa (IT)

(72) Inventors: Georgios Sakas, Darmstadt (DE); Velizar Kolev, Darmstadt (DE); Stefano De Beni, Genoa (IT); Leonardo Forzoni, Pistoia (IT)

(73) Assignees: MedCom Gesellschaft für medizinische Bildverarbeitung mbH, Darmstadt (DE); ESAOTE S.p.A., Genoa (IT)

( * ) Notice: Subject to any disclaimer, the term of this patent is extended or adjusted under 35 U.S.C. 154(b) by 63 days.

(21) Appl. No.: 15/158,039

(22) Filed: May 18, 2016

(65) Prior Publication Data
US 2016/0379368 A1 Dec. 29, 2016

(30) Foreign Application Priority Data
May 19, 2015 (DE) .......... 10 2015 209 143

(51) Int. Cl.
*G06K 9/00* (2006.01)
*A61B 34/20* (2016.01)

(52) U.S. Cl.
CPC ...... *A61B 34/20* (2016.02); *A61B 2034/2065* (2016.02); *G06T 2207/10028* (2013.01);
(Continued)

(58) Field of Classification Search
CPC .......... A61B 34/20; A61B 34/70; A61B 6/12; A61B 6/481; A61B 6/504; A61B 6/5247; A61B 6/463; A61B 6/464; A61B 6/465; A61B 6/4417; A61B 8/0833; A61B 8/0841; A61B 8/12; A61B 8/4245; A61B 8/4254; A61B 8/4263; A61B 8/5261; A61B 8/5238; A61B 8/461; A61B 8/463; A61B 8/464; A61B 8/465; A61B 8/466; A61B 8/469; A61B 8/483; A61B 17/3403; A61B 90/36;
(Continued)

(56) References Cited

U.S. PATENT DOCUMENTS 5,274,551 A * 12/1993 Corby, Jr. ............. A61B 6/12
                                                        348/45
6,733,458 B1 * 5/2004 Steins .................. A61B 8/0833
                                                        600/461
(Continued)

FOREIGN PATENT DOCUMENTS

EP         2 160 978 A1    10/2010

*Primary Examiner* — Jose Couso
(74) *Attorney, Agent, or Firm* — Frank J. Bonini, Jr.; John F. A. Earley, III; Harding, Earley, Follmer & Frailey, PC

(57) ABSTRACT

The present invention pertains to a method for image-assisted navigation, wherein an imaging specification for imaging a point in a three-dimensional system of coordinates in a point in a two-dimensional system of coordinates is determined, wherein a location of the imaging device is detected, and wherein the location of the imaging device is displayed in the two-dimensional reference image (RB).

19 Claims, 2 Drawing Sheets

Figure 1:
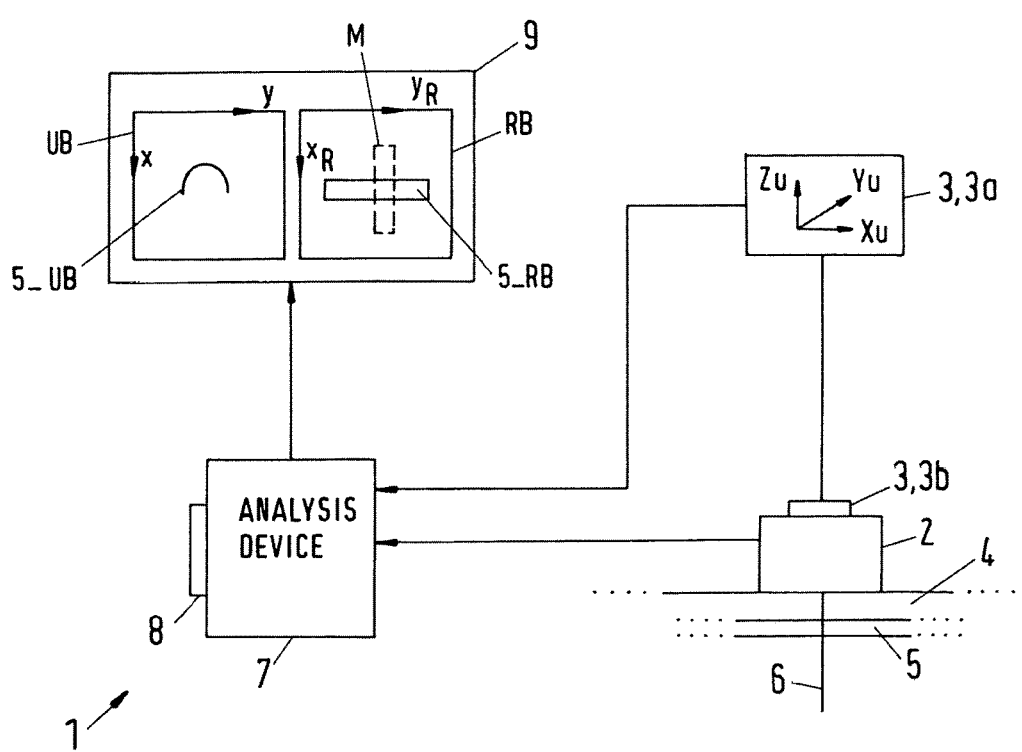

(52) U.S. Cl.
CPC ............... *G06T 2207/10121* (2013.01); *G06T 2207/10132* (2013.01); *G06T 2207/30004* (2013.01)

(58) Field of Classification Search
CPC ...... A61B 2034/107; A61B 2034/2051; A61B 2034/2063; A61B 2034/2065; A61B 2034/2055; A61B 2090/364; A61B 2090/365; A61B 2090/376; A61B 2090/378; A61B 2017/3413; G06T 7/38; G06T 5/50; G06T 11/003; G06T 15/08; G06T 2207/30004; G06T 2210/41; G06T 2219/028; G06T 7/0012; G06T 7/0014; Y10S 128/915; Y10S 128/916; A61N 2005/1058; A61N 2005/1059; A61N 5/1049; G06K 9/6289; G06K 2017/009; G06K 2209/05; G06K 2209/057; H04N 2201/0079; G06F 19/30; G06F 19/321; G06F 19/324; G06F 19/3406; G06F 19/3437; G06F 17/00; G06F 17/5009; G06F 11/3089; G06F 11/3093
See application file for complete search history.

(56) References Cited

U.S. PATENT DOCUMENTS

| | | | |
|---|---|---|---|
| 8,000,442 B2* | 8/2011 | Lachaine | A61B 8/00 378/65 |
| 8,126,239 B2* | 2/2012 | Sun | A61B 6/12 382/131 |
| 8,303,505 B2* | 11/2012 | Webler | G06F 19/3437 600/437 |
| 8,320,653 B2* | 11/2012 | Holsing | A61B 90/36 382/131 |
| 9,626,803 B2* | 4/2017 | Park | G06T 19/006 |
| 9,651,662 B2* | 5/2017 | Kruecker | G01S 15/899 |
| 2011/0184684 A1* | 7/2011 | Li | A61B 90/36 702/94 |
| 2014/0343404 A1* | 11/2014 | Razzaque | A61B 8/0841 600/424 |
| 2015/0016586 A1* | 1/2015 | Maurer, Jr. | G06T 7/0014 378/5 |
| 2015/0182191 A1* | 7/2015 | Caluser | A61B 8/5246 600/440 |
| 2017/0165008 A1* | 6/2017 | Finley | A61B 34/20 |

* cited by examiner

METHOD FOR DETERMINING AN IMAGING SPECIFICATION AND IMAGE-ASSISTED NAVIGATION AS WELL AS DEVICE FOR IMAGE-ASSISTED NAVIGATION

BACKGROUND OF THE INVENTION

1. Field of the Invention

The present invention pertains to a method for determining an imaging specification, especially for use in image-assisted navigation. The present invention also pertains to a method for image-assisted navigation as well as to a device for image-assisted navigation.

2. Brief Description of the Related Art

Within the framework of image-based examinations of examination objects, especially of parts of the human body, it may be advantageous, especially for inexperienced users, to be assisted in the spatial association of imaged structures in an image to predetermined areas or sections of the examination object.

Carrying out an imaging, especially in the medical field, by means of ultrasound is known. However, ultrasound images can be analyzed by inexperienced users with difficulty only. In particular, an association of structures of the examination object imaged in the ultrasound image to actual anatomical structures may be difficult.

Further, various imaging methods using ultrasound, e.g., imaging by generating a fluoroscopic image, especially by means of an X-ray method, are also known. These images generated in this way may be easier to analyze especially for inexperienced users.

Therefore, the technical problem is presented to create a method and a device for image-assisted navigation, which make possible a simplified spatial association of imaged structures to areas of an examination object especially for an inexperienced user. Further, the technical problem is presented to create a method for determining an imaging specification, which makes it possible to carry out the method for image-assisted navigation with simple computations and in a reliable manner.

SUMMARY OF THE INVENTION

A method for determining an imaging specification is provided. The imaging specification is used for imaging a point in a three-dimensional system of coordinates into a point in a two-dimensional system of coordinates. The imaging specification may be given, for example, in the form of a computer operation or a transformation.

The method may be used for image-assisted navigation, and particularly in medical image-assisted navigation. However, the method may, of course, also be used for image-assisted navigation in non-medical applications, for example, within the framework of the testing of materials.

BRIEF DESCRIPTION OF THE DRAWING FIGURES

Figure 2:
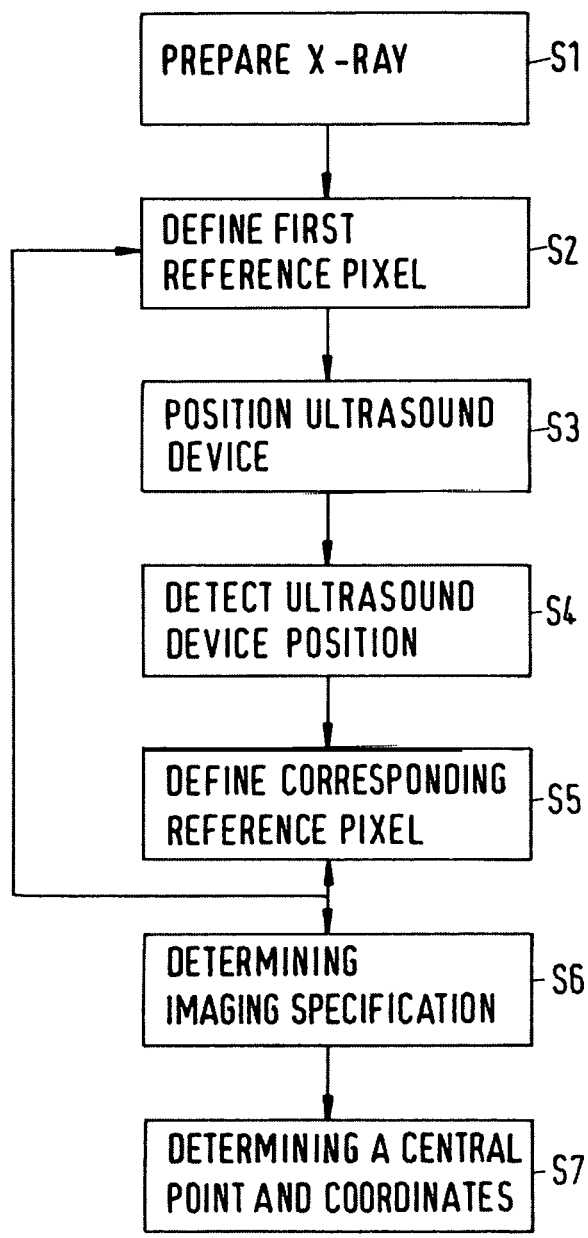

FIG. 1 shows a schematic block diagram of a device according to the present invention, and FIG. 2 shows a schematic flow chart of a method according to the present invention.

DETAILED DESCRIPTION OF THE INVENTION

The method comprises the following steps:

At least one two-dimensional reference image of an examination area is prepared in a first step. The examination area may designate, for example, an area or volume of an examination object, which is imaged into the two-dimensional reference image. The examination area may especially be a partial area of the human body. Nevertheless, the examination area may also be an area of a non-human examination object.

A first reference pixel in the first two-dimensional reference image in a system of coordinates of the first two-dimensional reference image is defined in a second step. The first reference pixel may completely or partly image a first reference structure of the examination object. In the sense of the present invention, a reference structure may designate an area or point of the examination object that can be identified in the reference image in as simple a manner as possible, for example, by a user or in an automated manner. The reference structure may also be designated as a landmark. It is also conceivable that the reference pixel is a geometric central point of an imaged area.

The definition may be carried out either manually or in an automated manner in this connection. In case of a manual definition, for example, a user may select the first reference pixel by means of at least one suitable input device. Nevertheless, it is also conceivable to define the reference pixel as a function of predetermined pixel properties in an automated manner. In this case, methods known to the person skilled in the art for image processing may be used.

An imaging device is arranged in a first location in a third step. The imaging device designates a device, by means of which structures in a detection area of the imaging device are imaged into an especially two-dimensional image.

In the sense of the present invention, the location designates a location in space, i.e., a position and/or orientation of the imaging device. The first location is selected here such that at least one part of the examination area with the first reference structure, which is imaged into the first reference pixel, is also imaged by means of the imaging device. The arranging can be carried out here either manually, e.g., by a user, or in an at least partly or even completely automated manner. For this, the imaging device may be arranged in the first location, for example, by means of a positioning device, and especially a positioning device operated in an actuator-assisted manner, for example, by a robot. The positioning device may be controlled in this case as a function of the images generated by the imaging device. The arranging may be carried out here either in a fully automated manner or by corresponding inputs of the user. However, it is, of course, also conceivable for the imaging device to be arranged in the first location in a purely manual manner, i.e., by means of a hand of the user.

The image detected in the first location by means of the imaging device thus images at least the first reference structure, but preferably a partial area of the examination area, which comprises the first reference structure. Thus, both the two-dimensional reference image and the image generated by the imaging device contain imaging information of the first reference structure.

The first location of the imaging device in a three-dimensional system of coordinates is detected in a further step. In this case, a detection may be carried out, for example, by a location-detecting device. The location-detecting device may be configured, for example, as a magnetic or optical tracking system. The three-dimensional system of coordinates may be a reference system of coordinates of the location-detecting device.

In a further step, a first corresponding reference pixel is defined in the image of the imaging device in the three-dimensional system of coordinates. This means that the coordinates of the corresponding reference pixel in the three-dimensional system of coordinates are determined. As already mentioned above, the definition may be carried out either manually or in an automated manner. Corresponding may mean that the reference pixel in the image of the imaging device images the same reference structure, which also images the reference pixel in the first two-dimensional reference image.

The detected first location may be associated with the image of the imaging device, which images the first reference structure, or with the corresponding reference pixel.

The detection of the location and the definition of the corresponding reference pixel may be carried out in one operation. It is also possible that the location of the imaging device is detected for determining the coordinates of the corresponding reference pixel in the three-dimensional system of coordinates.

At least one additional reference pixel is defined in the first two-dimensional reference image in a further step. In this case, an additional reference structure in the other reference pixel can be imaged at least partly or completely. For this, reference is made to the explanations on defining the first reference pixel.

The imaging device is arranged in another location in a further step such that at least one part of the examination area is imaged with the other reference structure, which is imaged in the other reference pixel. In this case, reference can be made to the explanations on arranging the imaging device in the first location. The other location may be different from the first location.

The other location of the imaging device in the three-dimensional system of coordinates is detected in a further step. In a further step, another corresponding reference pixel is defined in the image of the imaging device in the three-dimensional system of coordinates. For this as well, reference can be made to the explanations on the first location and on the first corresponding reference image.

The detected other location may be associated with the image of the imaging device, which images the other reference structure, or with the other corresponding reference pixel.

An imaging specification for imaging a point in the three-dimensional system of coordinates into a point in the two-dimensional system of coordinates is determined in a further step.

The imaging specification may be determined here as a function of the two-dimensional coordinates of the reference pixels in the reference image and as a function of the corresponding three-dimensional coordinates of the corresponding reference pixels in the three-dimensional system of coordinates.

Of course, the determination of the imaging specification also includes the determination of a scale.

As will still be explained in detail below, the definition of two pairs of pixels is sufficient for the determination of the imaging specification. Of course, a definition of more than two pairs of pixels is advantageous. In this case, a pair of pixels designates the pair consisting of the reference pixel in the two-dimensional reference image and the corresponding reference pixel in the three-dimensional system of coordinates.

To define a corresponding reference pixel in the three-dimensional system of coordinates, an imaging specification for imaging a pixel in the image generated by the imaging device, which may likewise be especially a two-dimensional image, may be previously known in the three-dimensional system of coordinates. This may mean that a calibration of the imaging device was carried out in relation to the three-dimensional system of coordinates. Thus, various pixels in the image of the imaging device may be associated with various coordinates in the three-dimensional system of coordinates.

If the imaging specification is known, then one, a plurality or all pixels in an image generated by the imaging device in a desired location may be associated with a corresponding pixel in the reference image. This may mean that the corresponding pixel in the reference image is calculated as a function of the current location of the imaging device and as a function of a coordinate of a point in the image of the imaging device. As will be explained in detail below, this pixel or an area around this pixel may be displayed to the user in the reference image, for example, by a crossfading, a highlighting or another visual effect.

Thus, it appears advantageously that a user can associate one, a plurality or all pixels generated by the imaging device and thus structures imaged in the image of the imaging device with corresponding structures in the reference image as well. This simplifies an orientation in space during the image-assisted examination of the examination area for the user.

The two-dimensional reference image is a projected image of the examination object, especially a fluoroscopic image, more particularly an X-ray, in a preferred embodiment. An especially simple orientation of the user is obtained as a result. As an alternative, but preferably cumulatively, the image of the imaging device is a sectional image of the examination area, especially a sound image, and more particularly an ultrasound image. The imaging device may thus be an ultrasound device or an ultrasound system.

The image of the imaging device may be, for example, an image generated in real time.

It is thus advantageously made possible to combine the information of an ultrasound image with the information of an X-ray.

The reference image may be especially an image generated before carrying out the proposed method. Of course, the method may, however, also comprise the generation of a reference image, especially by means of a corresponding device, e.g., by means of a fluoroscopic device.

The two-dimensional reference image may, as an alternative, also be an angiographic image.

As a result, it appears advantageously that, based on experience, ultrasound images that are difficult to analyze especially for inexperienced users can be better interpreted with regard to their orientation in space by combining with the fluoroscopic image.

In another embodiment, a connection line between two reference pixels is determined in the reference image, wherein a corresponding line between corresponding reference pixels is determined in the three-dimensional system of coordinates. In this case, a point on the connection line in the reference image can be associated with any point on the corresponding connection line.

The connection line may especially designate a straight line of infinite length, on which the two reference pixels are arranged. This applies especially to the case, in which only two reference pixels and thus two pairs of pixels were determined.

If more than two pairs of pixels were determined, then the connection line between two reference pixels may also be given by a half-line. In this connection, an endpoint of such a half-line may be a reference pixel that is arranged on at least two connection lines.

A connection line may in this case, however, also be a section, wherein both endpoints of the section are each a reference pixel. This may especially be given in the case, in which both reference pixels lie on at least two connection lines different from one another.

In this case, the imaging specification can be determined in such a way that a point in the three-dimensional system of coordinates is projected onto the corresponding connection line, wherein the reference point projected onto the corresponding connection line is then converted to the connection line of the reference points in the reference image. This means that coordinates of the pixel projected onto the corresponding connection line are converted into coordinates on the connection line in the reference image.

A projection may take place, for example, such that that image on the corresponding connection line in the three-dimensional system of coordinates associated with the pixel in the three-dimensional system of coordinates, which has the minimal distance to this pixel, is determined.

For example, coordinates of a predetermined point in the image of the imaging device, for example, a central point, can thus be converted into coordinates in the two dimensional system of coordinates of the reference image in each location of the imaging device. A determination of the imaging specification that is computationally simple to implement is advantageously obtained as a result.

In another embodiment, at least three reference pixels that are different from one another are defined, wherein the at least three reference pixels do not lie on a straight line.

Especially two connection lines can thus be determined. A pixel in the three-dimensional system of coordinates can advantageously be accurately converted into a pixel in the reference image as a function of the three reference pixels. As will still be explained in detail below, the three reference pixels, not lying on a straight line, especially make it possible to determine a translation part of a transformation between the three-dimensional system of coordinates and the two-dimensional system of coordinates of the reference image.

In another embodiment, a reference pixel is an imaged point of a ligament or of a bone. In particular, the reference pixel may thus be an imaged point of a structure extending along a central center line. More particularly, the reference pixel may be an endpoint of this structure.

Another reference pixel may then be defined at another end of this structure. As a result, an accurate determination of the imaging specification is advantageously obtained, so that the imaging is possible even in case of different spatial locations and/or geometric conditions of the examination area during imaging into the reference image or into the image of the imaging device. It can be assumed that the length of a ligament or bone is independent of a posture. If, for example, an X-ray images an arm and shoulder part with the upper arm and the lower arm angled towards one another, then an imaging specification can also be reliably determined from the three-dimensional system of coordinates in this X-ray for the case that an ultrasound image images an arm stretched out or almost stretched out.

In another embodiment, the imaging device for imaging the reference structure is arranged in each case such that a central point of the image of the imaging device images the reference structure. The central point thus images the reference structure. This means, in other words, that fixed image coordinates in the image generated by the imaging device are associated with the corresponding reference pixel. These fixed image coordinates may then be converted into the three-dimensional system of coordinates as a function of the corresponding location of the imaging device, then by means of the predetermined transformation explained above. The definition of the corresponding reference pixel is advantageously simplified as a result.

As an alternative, the imaging device may be arranged such that a contact point of the image of the imaging device images the reference structure. Of course, any other point of the image of the imaging device that can be repeatedly reliably identified may also be selected.

In another embodiment, the imaging specification comprises only a translation part. This means that a position of the corresponding reference pixel in the three-dimensional system of coordinates can be associated with a position of the reference pixel in the reference image, wherein, however, the association is independent of an orientation of the imaging device. This means that only the position of a point in the three-dimensional coordinates in the reference image can be displayed correctly, but no information on the orientation of the imaging device.

In another embodiment, the imaging device for imaging the reference structure is arranged in each case with the same orientation or in each case with orientations that do not deviate from one another by more than a predetermined quantity. This means that the imaging device in any location in which the imaging device is arranged for defining a corresponding reference pixel in the image of the imaging device has the same orientation in the three-dimensional coordinate system. For this, the orientation of the imaging device can be determined and corresponding information can be displayed to a user, for example, on a display device. It is also possible to determine a deviation of a current orientation from the predetermined same orientation and to display to a user or issue positioning commands corresponding to a suitable positioning device as a function of the deviation.

In an alternative embodiment, the imaging device is arranged in each case with an orientation depending on a reference structure. In this case, the imaging device may be arranged, e.g., such that an abscissa of the image generated by the imaging device intersects a center line of the reference structure at right angles. Of course, other orientations depending on a reference structure are also conceivable.

In another embodiment, the method further comprises the following steps. In a further step, a first reference orientation is defined in the two-dimensional reference image in the system of coordinates of the two-dimensional reference image. Further, the imaging device is arranged such that the image of the imaging device is generated along the first reference orientation. In particular, an abscissa of the image of the imaging device can be arranged such that the abscissa projected into the system of coordinates of the reference image has the first reference orientation. This may be carried out, for example, while arranging the imaging device in the first location explained above.

Further, the location, and especially the orientation, of the imaging device in the three-dimensional system of coordinates is detected.

At least one other reference orientation in the two-dimensional reference image is defined in the system of coordinates of the two-dimensional reference image in a further step. Further, the imaging device is arranged such that the image of the imaging device is generated along the other reference orientation. This can be carried out, for example, while arranging the imaging device in the other location explained above. Further, the location, in particular the orientation, of the imaging device is detected.

The first reference orientation is different from the other reference orientation in this case.

Corresponding to the corresponding pairs of points explained above, at least two corresponding orientation pairs are determined as a result. An orientation portion of the imaging specification, especially the transformation matrix, can be determined as a function of these orientation pairs. The orientation portion advantageously makes possible the determination, especially calculation, of an orientation of the image of the imaging device, especially an orientation of the abscissa, in the system of coordinates of the two-dimensional reference image. Of course, more than two orientation pairs may preferably be determined.

The first reference orientation is preferably an orientation of the abscissa of the reference image. The other orientation is preferably an orientation of the ordinate of the reference image.

As a result, it appears advantageously that orientation information can also be displayed in the two-dimensional reference image especially in a method for image-assisted navigation.

A method for image-assisted navigation is also proposed. In the method, an imaging specification according to one of the embodiments explained in this disclosure is determined. Further, a location of the imaging device is detected, for example, by means of the location-detecting device explained above. Further, the location of a detection area of the imaging device in the two-dimensional reference image is displayed.

Only one position of the location of the detection area of the imaging device can be displayed in this case. Of course, it is, however, also conceivable to display both a position and an orientation of the location of the detection area of the imaging device.

The location of the detection area of the imaging device can especially be displayed such that at least one part, i.e., at least one pixel, in the reference image, is displayed, in which a structure is imaged, which is likewise located in the detection area of the imaging device (and thus is also imaged into the image of the imaging device). The location of the detection area of the imaging device can be displayed by the pixel, which corresponds to a selected pixel, for example, the central point, in the image of the imaging device, being displayed in the reference image.

In this case, a displaying comprises a visual highlighting, for example, a color marking, of a pixel, of an image line or of a two-dimensional image area in the reference image. The image area of the reference image, into which structures that are located in the detection area of the imaging device are imaged, is preferably bordered, for example, with a color and/or intensity-based border. A visually distinguishable marking may also be superimposed over such an image area.

The method for image-assisted navigation may, as explained above, also comprise the steps of generating the reference image. In summary, the method for image-assisted navigation is used for displaying a location of a detection area of an imaging device in the two-dimensional reference image. The method may, of course, also comprise the actuation of one or a plurality of display devices in order to display the reference image, the location of the detection area of the imaging device in the reference image and/or the image of the imaging device.

The method for image-assisted navigation is used especially for displaying a location of a detection area of an ultrasound device in a two-dimensional fluoroscopic image.

As a result, it appears advantageously that at least one pixel, but preferably an image area, in the two-dimensional reference image, into which the same structures are imaged, is displayed to a user, who, especially in real time, generates images of the imaging device. This makes possible a simplified orientation of the user.

The image generated by the imaging device, especially the image generated in real time, and the two-dimensional reference image, are displayed at the same time in a preferred embodiment. As explained above, the location of the detection area of the imaging device can be displayed in the two-dimensional reference image.

For example, the images can be displayed on a display device next to one another or one below the other, especially in different partial display areas of the display device.

Further, the location of the imaging device in the two-dimensional reference image may likewise be displayed in real time. This means that changes in the location of the imaging device are displayed in the reference image without time delay.

In another embodiment, the location of the detection area of the imaging device is only displayed if a minimal distance of a position of a selected pixel in the image of the imaging device from a connection line in the three-dimensional system of coordinates is shorter than a predetermined threshold value, for example, shorter than 0.03 m. A selected pixel in the image of the imaging device may be, for example, a position of a central point of the image of the imaging device. The connection line in the three-dimensional system of coordinates was already explained above.

Areas, in which an accurate imaging is not possible, may arise due to the above-explained, point-based recording of the three-dimensional system of coordinates onto the two-dimensional system of coordinates of the reference image. Due to the proposed embodiment, a displaying of the location of the detection area of the imaging device in the reference image is advantageously carried out only if a defined accuracy of the imaging from the three-dimensional system of coordinates into the two-dimensional system of coordinates of the reference image is guaranteed.

In another embodiment, a point of a connection line in the three-dimensional system of coordinates is determined, which has the most minimal distance from the selected pixel, for example, from the central point, from the contact point or another point, in the image of the imaging device in the three-dimensional system of coordinates. The location of the detection area of the imaging device in the two-dimensional system of coordinates is determined in this case as the pixel that corresponds to the point on the connection line in the three-dimensional system of coordinates. A computationally simple, but reliable imaging is obtained as a result.

A device for image-assisted navigation is also proposed. The device comprises at least one imaging device, especially an ultrasound system. The device further comprises at least one location-detecting device, wherein a location, i.e., a position and/or orientation, of the imaging device, especially of the ultrasound transducer, can be detected by means of the location-detecting device. The device further comprises at least one display device and at least one analysis device. Further, a two-dimensional reference image can be read by means of the device. For this, the device may have especially a suitable interface, for example, a data interface. It is, of course, also possible that the device also comprises a device for generating the two-dimensional reference image, for example, an X-ray unit.

Further, a method for image-assisted navigation according to one of the embodiments explained in this disclosure can be carried out by means of the device. The device is thus configured for carrying out the method. In this case, especially the analysis device can carry out a method for determining an imaging specification according to one of the embodiments explained in this disclosure.

Further, the device may comprise at least one input device, wherein a pixel in the two-dimensional reference image and/or in the image of the imaging device can be selected or defined by actuating the input device. The input device may be, for example, a keyboard and/or a mouse. The location of the imaging device in the three-dimensional system of coordinates and/or the definition and/or determination of the corresponding reference pixel in the image of the imaging device may also be carried out during the actuation of the input device.

The device may be configured here as an enhanced ultrasound device.

The present invention is explained in detail on the basis of an exemplary embodiment. In the figures, FIG. 1 shows a schematic block diagram of a device according to the present invention, and FIG. 2 shows a schematic flow chart of a method according to the present invention.

FIG. 1 shows a schematic block diagram of a device 1 for image-assisted navigation. The device 1 comprises an imaging device configured as an ultrasound device 2, and only the ultrasound transducer is shown. The device 1 further comprises a location-detecting device configured as a magnetic tracking system 3, wherein the tracking system 3 comprises a base station 3a and a sensor part 3b. The sensor part 3b is fastened to the ultrasound device 2 in this case.

A Cartesian, three-dimensional system of coordinates of the tracking system 3, which has the axes xU, yU, and zU, is schematically shown.

Further, an examination object 4, for example, a human lower arm, is shown. The examination object 4 contains a structure 5 to be imaged, for example, a bone. A detection area 6 of the ultrasound device 2, which is two-dimensional and extends into the image plane or out of the image plane, is likewise shown. A part of the structure 5 is located in the detection area 6 in this case.

The ultrasound device 2 or the detection area 6 of the ultrasound device 2 and the tracking system 3 are recorded. This means that a coordinate in the three-dimensional system of coordinates of the tracking system 3 can be unambiguously determined for any pixel in the two-dimensional image of the ultrasound device 2.

The ultrasound device 2 can be positioned here, for example, manually. A position and/or orientation of the ultrasound device 2, especially of the ultrasound transducer, can be changed in this case.

The ultrasound device 2 is connected for data processing to an analysis device 7, which is likewise a part of the device 1 according to the present invention. The tracking system 3 is likewise connected to the analysis device 7 for data processing.

The analysis device 7 has a data interface 8 for reading a reference image RB, which may especially be an X-ray. The reference image RB is in this case displayed on a display device 9 of the device 1 according to the present invention. Further, an abscissa yR and an ordinate xR of the reference image RB are shown.

Further, the image generated by the ultrasound system 2, i.e., an ultrasound image UB, is displayed on the display device 9, which is connected to the analysis device 7 for data processing. In this case, an abscissa y and an ordinate x of the ultrasound image UB are likewise displayed. The display device 9 may especially be a display screen.

It is schematically shown that in the reference image RB the structure 5 is imaged as imaged structure 5_RB. Correspondingly, in the ultrasound image UB the structure 5 is displayed as imaged structure 5_UB.

The analysis device 7 may in this case, as will still be explained in detail below, carry out a method for image-assisted navigation. Here, the location of the detection area 6 of the ultrasound device in the form of a rectangular marking area M is displayed in the reference image RB, which is displayed on the display device 9 next to the ultrasound image UB. In this case, the marking area M comprises the part of the reference image RB, in which the part of the structure 5 is imaged, which is located in the detection area 6 of the ultrasound device 2. This means that the structure 5_UB imaged in the ultrasound image UB corresponds to the part of the imaged structure 5_UB in the reference image RB arranged in the marking area M.

Not shown is that the device 1 comprises an input device, which can be used, for example, for defining points, which will still be explained below, or for triggering a detection of a location of the ultrasound device.

FIG. 2 schematically shows a flow chart of a method according to the present invention.

A two-dimensional reference image RB (see FIG. 1), for example, an X-ray, is prepared in a first step S1. This reference image RB can be read by the analysis device 7 shown in FIG. 1.

A first reference pixel in the reference image RB in a system of coordinates of the reference image RB, which is formed by the abscissa yR and ordinate xR of the reference image RB shown in FIG. 1, is defined in a second step S2. For example, a user may select and define the reference pixel by means of suitable input devices.

In a third step S3, the ultrasound device 2 (see FIG. 1), especially the transducer, is arranged in a first position such that the detection area 6 of the ultrasound device 2 detects a part of the structure 5, which is imaged by the defined reference pixel.

In a fourth step S4, the location, i.e., the position, of the ultrasound device 2, is detected by a tracking system 3 (see FIG. 1). For example, a user can trigger the detection by means of an actuation of a suitable input device.

A corresponding reference pixel in the ultrasound image UB in the three-dimensional system of coordinates, which is formed by the axes xU, yU, and zU of the tracking system 3 shown in FIG. 1, is defined in a fifth step S5. For example, a user can select and define the corresponding reference pixel by means of suitable input devices.

It is also possible that the arrangement in the first location is carried out such that the part of the structure 5, which is imaged by the defined reference pixel, is imaged by a predetermined point of the ultrasound image, for example, a central point. In this case, the corresponding pixel in the ultrasound image can be defined during the detection of the location without separate selection.

The sequence of steps between the second step S2 (inclusive) and the fifth step S5 (inclusive) is repeated until a desired number of pairs of reference pixels, which are different from one another, of reference pixels in the reference image RB and corresponding reference pixels in the ultrasound image UB were defined. The sequence of steps is, however, carried out at least twice.

An imaging specification for imaging a point in the three-dimensional system of coordinates in a point in the two-dimensional system of coordinates is determined in a sixth step S6.

After determining the imaging specification, a central point of the ultrasound image UB and of its coordinates in the three-dimensional system of coordinates is determined in a seventh step S7 in each location of the ultrasound device. The corresponding pixel in the reference image RB is then determined by means of the imaging specification. A marking area M, which has a rectangular configuration and the central point of which is the corresponding pixel, is then collimated in the reference image RB. The collimation may, however, only be carried out when a minimal distance of the current central point of the ultrasound image from a connection line between the corresponding reference pixels in the three-dimensional system of coordinates is shorter than a predetermined threshold value, for example, shorter than 0.03 m.

The invention claimed is:

1. A method for determining an imaging specification, wherein the method comprises the following steps:
preparing at least one two-dimensional reference image (RB) of an examination area (4),
defining a first reference pixel in the two-dimensional reference image (RB) in a system of coordinates of the two-dimensional reference image (RB),
arranging an imaging device in a first location such that at least one part of the examination area (4) is imaged with a first reference structure (5), which is imaged into the first reference pixel,
detecting the first location of the imaging device in a three-dimensional system of coordinates,
defining a first corresponding reference pixel in the image of the imaging device in the three-dimensional system of coordinates,
defining at least one other reference pixel in the two-dimensional reference image (RB),
arranging the imaging device in another location such that at least one part of the examination area (4) is imaged with another reference structure, which is imaged into the other reference pixel,
detecting the other location of the imaging device in the three-dimensional system of coordinates,
defining another corresponding reference pixel in the image of the imaging device in the three-dimensional system of coordinates, and
determining an imaging specification for imaging a point in the three-dimensional system of coordinates in a point in the two-dimensional system of coordinates;
characterized in that a connection line between two reference points in the reference image (RB) is determined, and a corresponding connection line between corresponding reference pixels in the three-dimensional system of coordinates is determined.

2. The method in accordance with claim 1, characterized in that the two-dimensional reference image (RB) is a projected image of the examination area (4) and/or the image of the imaging device is a sectional image of the examination area (4).

3. The method of claim 1, characterized in that at least three reference pixels, which are different from one another, are determined, wherein the at least three reference pixels do not lie on a straight line.

4. The method of claim 1, characterized in that a reference pixel is an imaged point of a ligament or of a bone.

5. The method of claim 1, characterized in that the imaging device for imaging a reference structure is arranged in each case such that a central point of the image of the imaging device images the reference structure.

6. The method of claim 1, characterized in that the imaging specification comprises only a translation part.

7. The method of claim 1, characterized in that the imaging device for imaging the reference structure (5) is arranged in each case with the same orientation or in each case with orientations, which deviate from one another by no more than a predetermined quantity, or in each case with an orientation depending on the reference structure.

8. The method of claim 1, characterized in that the method further comprises the following steps:
defining a first reference orientation in the two-dimensional reference image (RB) in the system of coordinates of the two-dimensional reference image (RB),
arranging an imaging device such that the image of the imaging device is generated along the first reference orientation,
detecting the location of the imaging device in the three-dimensional system of coordinates,
defining at least one other reference orientation in the two-dimensional reference image (RB) in the system of coordinates of the two-dimensional reference image (RB),
arranging an imaging device such that the image of the imaging device is generated along the other reference orientation, and
detecting the location of the imaging device in a three-dimensional system of coordinates.

9. A method for image-assisted navigation, wherein an imaging specification according to claim 1 is determined, wherein a location of the imaging device is detected, and wherein a location of a detection area of the imaging device is displayed in the two-dimensional reference image (RB).

10. The method in accordance with claim 9, characterized in that the image generated by the imaging device and the two-dimensional reference image (RB) are displayed at the same time.

11. The method in accordance with claim 9, characterized in that the location of the imaging device is displayed only if a minimal distance of a selected pixel in the image of the imaging device from a connection line in the three-dimensional system of coordinates is shorter than a predetermined threshold value.

12. The method in accordance with claim 9, characterized in that a point of a connection line in the three-dimensional system of coordinates, which has the most minimal distance from a selected pixel in the image of the imaging device, is determined, wherein the location of the detection area of the imaging device in the two-dimensional system of coordinates is determined as the pixel that corresponds to the point on the connection line in the three-dimensional system of coordinates.

13. A device for image-assisted navigation, wherein the device (1) comprises at least one image-detecting device, at least one location-detecting device for detecting the location of the image-detecting device, at least one display device (9) and at least one analysis device (7), wherein a two-dimensional reference image (RB) can be read by means of the device (1), and wherein the method according to claim 9 is carried out by means of the device.

14. The method of claim 3, characterized in that a reference pixel is an imaged point of a ligament or of a bone.

15. The method of claim 14, characterized in that the imaging device for imaging the reference structure is arranged in each case such that a central point of the image of the imaging device images the reference structure.

16. The method of claim 15, characterized in that the imaging specification comprises only a translation part.

17. The method of claim 16, characterized in that the imaging device for imaging the reference structure (5) is arranged in each case with the same orientation or in each case with orientations, which deviate from one another by no more than a predetermined quantity, or in each case with an orientation depending on the reference structure.

18. A method for determining an imaging specification, wherein the method comprises the following steps:
- preparing at least one two-dimensional reference image (RB) of an examination area (4),
- defining a first reference pixel in the two-dimensional reference image (RB) in a system of coordinates of the two-dimensional reference image (RB),
- arranging an imaging device in a first location such that at least one part of the examination area (4) is imaged with a first reference structure (5), which is imaged into the first reference pixel,
- detecting the first location of the imaging device in a three-dimensional system of coordinates,
- defining a first corresponding reference pixel in the image of the imaging device in the three-dimensional system of coordinates,
- defining at least one other reference pixel in the two-dimensional reference image (RB),
- arranging the imaging device in another location such that at least one part of the examination area (4) is imaged with another reference structure, which is imaged into the other reference pixel,
- detecting the other location of the imaging device in the three-dimensional system of coordinates,
- defining another corresponding reference pixel in the image of the imaging device in the three-dimensional system of coordinates, and
- determining an imaging specification for imaging a point in the three-dimensional system of coordinates in a point in the two-dimensional system of coordinates;
- characterized in that a connection line between two reference points in the reference image (RB) is determined, and a corresponding connection line between corresponding reference pixels in the three-dimensional system of coordinates is determined,
- the two-dimensional reference image (RB) is a projected image of the examination area (4) and/or the image of the imaging device is a sectional image of the examination area (4),
- at least three reference pixels, which are different from one another, are determined,
- wherein the at least three reference pixels do not lie on a straight line,
- a reference pixel is an imaged point of a ligament or of a bone,
- the imaging device for imaging the reference structure is arranged in each case such that a central point of the image of the imaging device images the reference structure,
- the imaging specification comprises only a translation part, and
- the imaging device for imaging the reference structure (5) is arranged in each case with the same orientation or in each case with orientations, which deviate from one another by no more than a predetermined quantity, or in each case with an orientation depending on the reference structure.

19. The method of claim 18, characterized in that the method further comprises the following steps:
- defining a first reference orientation in the two-dimensional reference image (RB) in the system of coordinates of the two-dimensional reference image (RB),
- arranging an imaging device such that the image of the imaging device is generated along the first reference orientation,
- detecting the location of the imaging device in the three-dimensional system of coordinates,
- defining at least one other reference orientation in the two-dimensional reference image (RB) in the system of coordinates of the two-dimensional reference image (RB),
- arranging an imaging device such that the image of the imaging device is generated along the other reference orientation, and
- detecting the location of the imaging device in a three-dimensional system of coordinates.

* * * * *